United States Patent
Mertens et al.

(10) Patent No.: US 6,831,142 B2
(45) Date of Patent: Dec. 14, 2004

(54) PULVERULENT, CROSSLINKED POLYMERS WHICH ABSORB AQUEOUS LIQUIDS AND BLOOD

(75) Inventors: Richard Mertens, Krefeld (DE); Harren Jörg, Krefeld (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 10/379,510

(22) Filed: Mar. 4, 2003

(65) Prior Publication Data

US 2004/0176557 A1 Sep. 9, 2004

Related U.S. Application Data

(63) Continuation of application No. PCT/EP01/06362, filed on Sep. 4, 2000.

(30) Foreign Application Priority Data

Sep. 4, 2000 (DE) .......................................... 100 43 706

(51) Int. Cl.[7] .............................. C08F 8/42; C08F 20/06
(52) U.S. Cl. ............................ 526/328.5; 526/317.1; 525/55; 525/57; 525/61; 525/244; 525/246; 525/249; 525/253
(58) Field of Search ......................... 526/317.1, 328.5; 525/55, 57, 61, 244, 246, 249, 253, 301, 329.7, 330.2, 370

(56) References Cited

U.S. PATENT DOCUMENTS

| 4,043,952 A | 8/1977 | Ganslaw et al. |
| 4,076,663 A | 2/1978 | Masuda et al. |
| 4,286,082 A | 8/1981 | Tsubakimoto et al. |
| 4,340,706 A | 7/1982 | Obayashi et al. |
| 4,640,810 A | 2/1987 | Laursen et al. |
| 4,771,105 A * | 9/1988 | Shirai et al. .............. 525/54.23 |
| 5,409,771 A * | 4/1995 | Dahmen et al. ............ 428/327 |
| 5,669,894 A | 9/1997 | Goldman et al. |

FOREIGN PATENT DOCUMENTS

| EP | 0 233 067 A2 | 8/1987 |
| EP | 0 339 461 A1 | 11/1989 |
| EP | 0 574 260 A1 | 12/1993 |
| EP | 0 668 080 A2 | 8/1995 |
| EP | 0 712 659 A1 | 5/1996 |
| EP | 0 837 076 A2 | 4/1998 |
| EP | 0 850 615 A1 | 7/1998 |
| EP | 0 889 063 A1 | 1/1999 |
| WO | WO 95/22356 | 8/1995 |
| WO | WO 96/05234 | 2/1996 |
| WO | WO 97/12575 | 4/1997 |
| WO | WO 98/48857 | 11/1998 |
| WO | WO 98/49221 | 11/1998 |
| WO | WO 99/49905 | 10/1999 |

* cited by examiner

Primary Examiner—David W. Wu
Assistant Examiner—Satya Sastri
(74) Attorney, Agent, or Firm—Smith Moore LLP

(57) ABSTRACT

The invention relates to absorptive, crosslinked polymers which are based on partly neutralized, monoethylenically unsaturated monomers carrying acid groups, and have improved properties, in particular in respect of their capacity for transportation of liquids in the swollen state, and which have been after-crosslinked on their surface at temperatures of at least 150° C. with a combination of polyol as after-crosslinking compound and a cation in the form of an aqueous solution.

22 Claims, No Drawings

PULVERULENT, CROSSLINKED POLYMERS WHICH ABSORB AQUEOUS LIQUIDS AND BLOOD

This application is a continuation of International Application No. PCT/EP01/06362, internationally filed Sep. 4, 2000.

FIELD OF THE INVENTION

The invention relates to pulverulent, crosslinked polymers which absorb water, aqueous liquids and blood (superabsorbers) and have improved properties, in particular an improved retention and an improved retention capacity for liquids under pressure and an improved capacity for transportation of liquids, their preparation and their use as absorbents in hygiene articles and in industrial fields.

BACKGROUND OF THE INVENTION

Superabsorbers are water-insoluble, crosslinked polymers which are capable of absorbing large amounts of aqueous liquids and body fluids, such as e.g. urine or blood, with swelling and the formation of hydrogels, and of retaining them under a certain pressure. As a result of these characteristic properties, these polymers are chiefly used for incorporation into sanitary articles, such as e.g. babies' nappies, incontinence products or sanitary towels.

The superabsorbers which are currently commercially available are substantially crosslinked polyacrylic acids or crosslinked starch-acrylic acid graft polymers, in which some of the carboxyl groups are neutralized with sodium hydroxide solution or potassium hydroxide solution.

For aesthetic reasons and from environmental aspects, there is an increasing trend to make sanitary articles, such as babies' nappies, incontinence products and sanitary towels, ever smaller and thinner. To ensure a constant total retention capacity of the sanitary articles, this requirement can be met only by reducing the content of large-volume fluff. As a result of this, further tasks fall to the superabsorbers in respect of transportation and distribution of liquid, which can be summarized as permeability properties.

In the case of superabsorber materials, permeability is understood as meaning the capacity for transportation and three-dimensional distribution of added liquids in the swollen state. This process proceeds in the swollen superabsorber gel by a capillary transportation through intermediate spaces between the gel particles. Transportation of liquid through swollen superabsorber particles itself follows the laws of diffusion and is a very slow process which plays no role in the distribution of the liquid in the use situation of the sanitary article. In superabsorber materials which cannot effect capillary transportation because of a lack of gel stability, separation of the particles from one another, avoiding the gel blocking phenomenon, has been ensured by embedding these materials into a fiber matrix. In nappy constructions of the new generation, there is only little fiber material, or none at all, in the absorber layer to assist in transportation of the liquid. The superabsorbers used here must accordingly have a sufficiently high stability in the swollen state so that the swollen gel still has a sufficient amount of capillary spaces through which liquid can be transported.

To obtain superabsorber materials with a high gel strength, on the one hand the degree of crosslinking of the polymer can be increased, which necessarily results in a reduction in the swellability and the retention capacity. An optimized combination of various crosslinking agents and comonomers, as described in the patent specification DE 196 46 484, is indeed capable of improving the permeability properties, but not to a level which allows, for example, incorporation of a layer which optionally comprises only superabsorbers in a nappy construction.

Methods for surface after-crosslinking of the polymer particles can furthermore be used. In so-called after-crosslinking, the carboxyl groups of the polymer molecules on the surface of the superabsorber particles are reacted with various after-crosslinking agents which can react with at least two of the carboxyl groups close to the surface. In addition to increasing the gel strength, the ability to absorb liquid under pressure is greatly improved in particular, since the known phenomenon of gel blocking, in which swollen polymer particles stick together and as a result a further absorption of liquid is prevented, is suppressed.

The surface treatment of liquid-absorbing resins is already known. To improve dispersibility, ionic complexing of the carboxyl groups close to the surface with polyvalent metal cations is proposed in U.S. Pat. No. 4,043,952. The treatment is carried out with salts of polyvalent metals dispersed in organic, optionally water-containing solvents (alcohols and other organic solvents).

An after-treatment of superabsorber polymers with reactive surface-crosslinking compounds (alkylene carbonates) to increase the absorptive ability for liquids under pressure is described in DE-A40 20 780. A surface after-crosslinking of superabsorbent polymers with polyfunctional crosslinking agents, such as polyvalent metal compounds, in the presence of an inert, inorganic powder, such as $SiO_2$, to improve the absorption properties and to produce a non-tacky gel of the polymer particles is described in DE-A-35 03 458.

According to EP-A-0 574 260, superabsorbent polymers with a low residual monomer content which does not change decisively even by surface crosslinking are obtained if certain conditions are maintained during the polymerization and the after-crosslinking is carried out with conventional polyfunctional crosslinking agents, such as polyols, alkylene carbonates and polyvalent metal salts, under conventional conditions.

The after-crosslinked polymers show a good absorption without the use of pressure. According to EP-A-0 889 063, superabsorbent polymers which are already surface-crosslinked can be treated against free-radical degradation by body fluids, in particular L-ascorbic acid, by after-treatment with a compound of titanium or zirconium and a compound which chelates these metal compounds.

EP 0 233 067 describes water-absorbing resins which are crosslinked on the surface and are obtained by reaction of a superabsorbent polymer powder with 1–40 wt. %, based on the polymer powder, of an aluminium compound. A mixture of water and diols, which is said to make the use of lower alcohols as solvents superfluous, is used as the treatment solution. 100 parts by wt. of crosslinking agent solution are applied to 100 to 300 parts by weight of absorber. The diols (e.g. polyethylene glycol 400 and 2000, 1 ,3-butanediol or 1,5-pentanediol) added to the reaction medium of water also serve to prevent lumping together of the superabsorber during treatment with the large amounts of aqueous treatment solution used here. The solvent is removed in a subsequent drying step at 100° C. The polymers treated in this way have an inadequate level of properties, and an improvement in the absorptive ability under pressure is not achieved. Furthermore, treatment with large amounts of treatment solution cannot be carried out economically in modem, continuously operating processes.

WO 96/05234 describes a process for the treatment of superabsorbent polymers, according to which the surface of the absorber particles, which contain at least 10 wt. % water, was treated with a crosslinked layer obtained by a reaction of a reactive, hydrophilic polymer or a reactive organometallic compound with an at least bifunctional crosslinking agent at temperatures below 100° C. Metal salts are not mentioned. The metal compounds employed must be able to react with the functional groups of the crosslinking agent. Organometallic compounds are therefore recommended as the metal compounds, and should be present in a weight ratio of 0.1 to 30 to the crosslinking compound. The polymers obtained are said to have a balanced ratio of absorption, gel strength and permeability, the measurement values stated being determined under less critical conditions. Thus, for example, the absorption and the permeability are determined without any pressure loading. A disadvantage of this known process is the use of solvents and toxically unacceptable crosslinking reagents, such as e.g. the polyimines, alkoxylated silane or titanium compounds and epoxides mentioned as preferred.

According to WO 95/22356 and WO 97/12575, an improvement in the permeability and liquid transportation properties is achieved by an appropriate treatment of commercially obtainable superabsorber polymers with amino polymers in organic solvents. The serious disadvantage of the process described here, in addition to the use of toxicologically unacceptable polyamines and polyimines, lies in the use of large amounts of organic solvents, which are necessary for the treatment of the polymers. The associated safety aspect and cost outlay rules out a production on a large industrial scale. In addition to the toxicological unacceptability of these treatment agents, it is furthermore to be taken into account that they also tend to decompose under the high after-crosslinking temperatures, which manifests itself, inter alia, in a yellowing of the absorber particles.

To prepare water-absorbing polymers with an improved abrasion resistance, the Japanese laid-open specification JP-A-09124879 is directed to after-crosslinking of the surface with polyfunctional crosslinking agents, the water content of the polymer particles again being adjusted to 3–9 wt. % after the surface-crosslinking and it being possible for this amount of water to contain inorganic compounds, such as metal salts.

Superabsorbent polymers which, according to WO 98/48857, are brought into contact in particle form with polyvalent metal salts by dry mixing and are then provided with a certain amount of a liquid binder, such as water or polyols, are said to have an improved gel blocking during absorption of aqueous liquids. The polymer particles can be subjected to after-crosslinking of the surface before this treatment.

To minimize the tendency of superabsorbent after-crosslinked polymer particles towards agglomeration due to electrostatic charging, WO 98/49221 recommends re-moistening of the polymer particles to the extent of up to 10 wt. % water with an aqueous additive solution. These aqueous solutions can contain mono- or polyvalent ions or propoxylated polyols. It is also possible for the polymer particles already to be brought into contact with the aqueous additive solution before the after-treatment of the surface, as a result of which a more uniform distribution of the agent for after-treatment of the surface is said to be achieved.

No indication that, while retaining a high retention capacity and absorptive ability for liquid under pressure in the after-crosslinking stage, the permeability properties can also be increased drastically is to be found from the prior art described above.

SUMMARY OF THE INVENTION

The object of the present invention is to provide superabsorbent polymers which have an improved combination of properties, in particular not only a high absorptive ability under pressure, but also combine the conventionally opposing properties of a high retention capacity and a good permeability, i.e. have a level of the combination of properties at which, in addition to a retention value of at least about 25 g/g, at least an SFC value of at least, $45 \cdot 10^{-7}$, preferably at least $50 \cdot 10^{-7}$ cm$^3$ sec/g is present. In particular, an object is to provide superabsorbent polymers which are suitable above all for use in very thin nappy constructions with a very high superabsorber content. For this case, polymers with retention values of at least about 25 g/g and permeability values of SFC more than $70 \times 10^{-7}$ cm$^3$ s/g are required in particular.

A further object of the invention was to discover preparation processes for such superabsorbent polymers which can be carried out simply, economically and reliably, give a uniform product quality and in which in particular small amounts of solvent are used and where possible organic solvents are avoided. It should furthermore be possible to carry out the processes without the use of toxicologically unacceptable substances.

The object according to the invention is achieved by providing a pulverulent polymer which is after-crosslinked on the surface, absorbs water, aqueous or serous liquids and blood and is built up from a) 55–99.9 wt. % of polymerized, ethylenically unsaturated monomers which contain acid groups and are neutralized to the extent of at least 25 mol %, b) 0–40 wt. % of polymerized, ethylenically unsaturated monomers which can be copolymerized with a), c) 0.1–5.0 wt. % of one or more polymerized-in crosslinking agents, d) 0–30 wt. % of a water-soluble polymer the sum of the amounts by weight of a) to d) being 100 wt. %, the polymer has been coated with e) 0.01 to 5 wt. %, based on the polymer, of at least one polyol as an agent for after-crosslinking of the surface in an aqueous solution and with f) 0.001–1.0 wt. %, based on the polymer, of a cation in the form of a salt dissolved in an aqueous solution and has been heated to an after-crosslinking temperature in the range from about 150 to 250° C., the weight ratio of salt to polyol being in the range from 1:0.8 to 1:4 and the total amount of aqueous solutions having a range from 0.5 to 10 wt. %, based on the polymer, excluding crosslinked partly neutralized polyacrylic acid which has been treated with $Al_2(SO_4)_3$ and glycerol in a weight ratio of 1:1 or with $Al_2(SO_4)_3 \cdot 16H_2O$ and polyethylene glycol in a weight ratio of 1:1.8 or with $Al_2(SO_4)_3 \cdot 14H_2O$ and ethylene glycol in a weight ratio of 1:2 or with $Al_2(SO_4)_3 \cdot 18H_2O$ and ethylene glycol in a weight ratio of 1:2 or $Al_2(SO_4)_3 \cdot 18H_2O$ and propylene glycol in a weight ratio of 1:1.6.

DETAILED DESCRIPTION OF THE INVENTION

Surprisingly, by coating a particulate absorbent polymer with an aqueous solution of a polyol which has reacted with the molecular groups close to the surface, preferably with the carboxyl groups, in the presence of a cation of a water-soluble salt while heating in the range from 150 to 250° C., in fact a superabsorbent polymer with a significant improvement in the permeability properties coupled with a very good retention capacity results if the water-soluble salt is present in a certain weight ratio to the polyol and the amount of water added lies within the limits according to the invention.

The treatment with an aqueous solution of the combination, according to the invention, of after-crosslinking components leads completely unexpectedly to the desired results, that is to say obtaining of polymers with a high retention capacity, even under pressure, with simultaneously excellent permeability properties. Successive separate use of the aqueous solution of the organic after-crosslinking agents and the aqueous salt solution with the particular heating does not lead to comparably good product characteristics.

The sole use of a polyol as the organic after-crosslinking agent in aqueous solution indeed leads to products with a high retention capacity, high gel strength and high absorptive ability under pressure. However, a significant increase in the permeability in the swollen state can be achieved only by a correspondingly higher degree of crosslinking of the polymers during the polymerization or a more intense after-crosslinking (increased amounts of after-crosslinking agents or more drastic conditions) and the associated loss of retention capacity.

Sole after-crosslinking with cations of high positive charge density also does not lead to polymers with the desired combination of properties. In particular, no satisfactory values for the absorption of liquid under pressure and no good permeability properties can be achieved. An improvement in the stability under pressure or moreover the liquid transportation properties in the swollen state is not achieved.

The required properties also cannot be achieved by a small amount of polyol and large amounts of cations.

According to the invention, polyols which react with the COOH groups of the polymer close to the surface are employed as the organic after-crosslinking component e) of claim 1.

Polyols which are preferably used are aliphatic polyhydroxy compounds with preferably a molecular weight of not more than 250, such as $C_2$-$C_8$-alkylene diols, such as e.g. ethylene glycol, 1,3-propanediol, 1,4-butanediol, 1,5-pentanediol, 1,6-hexanediol and dianhydrosorbitol, $C_2$-$C_8$-alkylene triols, such as e.g. glycerol and trimethylolpropane, hydroxy compounds of higher functionality, such as e.g. pentaerythritol and sugar alcohols, such as e.g. sorbitol, and di- and polyalkylene glycols, such as e.g. diethylene glycol, dipropylene glycol, triethylene glycol, tetraethylene glycol, tetrapropylene glycol, polyethylene glycol and polypropylene glycol, and polyglycols based on 2 or more different alkoxides, such as e.g. a polyglycol of ethylene oxide and propylene oxide units.

The organic after-crosslinking components or mixtures thereof are employed in amounts of 0.01–5 wt. %, preferably 0.1–2.5 wt. %, and more preferably 0.5 to 1.5 wt. %, based on the polymer to be crosslinked.

According to the invention, the aqueous solutions of water-soluble salts, the anions of which are chlorides, bromides, sulfates, carbonates, nitrates, phosphates or organic anions, such as acetates and lactates, are preferably employed as component f) of claim 1 for crosslinking the carboxylate groups close to the surface. The cations of the salts are preferably derived from mono- and polyvalent cations, the monovalent in particular from alkali metals, such as potassium, sodium and lithium, lithium being preferred. Divalent cations which are used according to the invention are derived from zinc, beryllium and alkaline earth metals, such as magnesium, calcium and strontium, magnesium being preferred. Further examples of cations of higher valency which can be employed according to the invention are cations of salts of aluminium, iron, chromium, manganese, titanium, zirconium and other transition metals and double salts of such cations or mixtures of the salts mentioned. Trivalent cations and cations of higher valency are preferably employed, and of these in particular water-soluble, inorganic salts, and of these aluminium salts and alums and various hydrates thereof, such as e.g. $AlCl_3 \times 6H_2O$, $NaAl(SO_4)_2 \times 12H_2O$, $KAl(SO)_4 \times 12H_2O$ or $Al_2(SO_4)_3 \times 14. 18H_2O$ or $Al(NO_3)_3 \times 9H_2O$. $Al_2(SO_4)_3$ or $Al(NO_3)_3$ and their hydrates are preferably used. The salt component is employed in amounts, calculated for the cation, of 0.001–1.0 wt. %, preferably 0.005–0.5 wt. %, and preferably 0.01–0.2 wt. %, based on the polymer. The preferred weight ratio of water-soluble salt to after-crosslinking agent is preferably 1:1 to 1:3.5, and more preferably 1:1.2 to 1:2.5.

The water-absorbing polymer which is surface-crosslinked according to the invention is obtained, inter alia, by polymerization of a) 55–99.9 wt. % of a mono-ethylenically unsaturated monomer with acid groups. Monomers containing carboxyl groups, such as e.g. acrylic acid, methacrylic acid or 2-acrylamido-2-methylpropanesulfonic acid, or mixtures of these monomers are preferred here. It is preferable for at least 50 wt. %, and more preferably at least 75 wt. % of the acid groups to be carboxyl groups. The acid groups are neutralized to the extent of at least 25 mol %, i.e. they are present as sodium, potassium or ammonium salts. The degree of neutralization is preferably at least 50 mol %. Polymers which have been obtained by polymerization of acrylic acid or methacrylic acid, the carboxyl groups of which are neutralized to the extent of 50–80 mol %, in the presence of crosslinking agents are preferred.

Further monomers b) which can be used for the preparation of the absorbent polymers according to the invention are 0–40 wt. % of ethylenically unsaturated monomers which can be copolymerized with a), such as e.g. acrylamide, methacrylamide, hydroxyethyl acrylate, dimethylaminoalkyl (meth)-acrylate, dimethylaminopropylacrylamide or acrylamidopropyltrimethylammonium chloride. More than 40 wt. % of these monomers can impair the swellability of the polymers.

All compounds which carry at least two ethylenically unsaturated double bonds or one ethylenically unsaturated double bond and one functional group which is reactive towards acid groups of the monomers a) or several functional groups which are reactive towards acid groups can be used as the crosslinking component c) which is present during the polymerization of a) and b). Examples which may be mentioned are: aliphatic amides, such as e.g. methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, tetraallyloxyethane, triallylamine, tetraallylethylenediamine and allyl esters of phosphoric acid or phosphorous acid, and furthermore monomers which are capable of crosslinking, such as N-methylol compounds of unsaturated amides, such as of methacrylamide or acrylamide, and the ethers derived therefrom. Mixtures of the crosslinking agents mentioned can also be employed. The content of the crosslinking comonomers is 0.1 to 5 wt. %, and preferably 0.01 to 3.0 wt. %, based on the total amount of the monomers.

The absorbent polymers according to the invention can comprise as water-soluble polymers d) 0–30 wt. % of water-soluble polymers, such as partly or completely hydrolysed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0–30 wt. %, preferably 0–5 wt. %, based on the total amount of components a) to d). The water-soluble polymers, preferably synthetic polymers, such as polyvinyl alcohol, can also serve as a graft base for the monomers to be polymerized.

The usual initiators, such as e.g. azo or peroxo compounds, redox systems or UV initiators, (sensitizers), are used for initiation of the free-radical polymerization.

The polymers according to the invention are preferably prepared by two methods.

According to the first method, the partly neutralized monomer a), preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously. The prior art has a broad spectrum of possible variations in respect of the concentration ratios, temperatures and nature and amount of the initiators. Typical processes are described in the following publications: U.S. Pat. No. 4,286,082, DE 27 06 135 and U.S. Pat. No. 4,076,663, the corresponding disclosure of which is incorporated by reference.

Inverse suspension and emulsion polymerization can also be used for preparation of the products according to the invention. According to these processes, an aqueous, partly neutralized solution of monomers a), preferably acrylic acid, is dispersed in a hydrophobic, organic solvent with the aid of protective colloids and/or emulsifiers and the polymerization is started by free radical initiators. The crosslinking agents either are dissolved in the monomer solution and are metered in together with this, or are added separately and optionally during the polymerization. The addition of a water-soluble polymer d) as the graft base optionally takes place via the monomer solution or by direct introduction into the oily phase. The water is then removed azeotropically from the mixture and the polymer is filtered off and optionally dried. Crosslinking can be carried out by polymerizing-in a polyfunctional crosslinking agent dissolved in the monomer solution and/or by reaction of suitable crosslinking agents with functional groups of the polymer during the polymerization steps. The processes are described, for example, in the publications U.S. Pat. No. 4,340,706, DE 37 13 601, DE 28 40 010 and WO 96/05234, the corresponding disclosure of which are incorporated by reference.

Drying of the polymer gel is carried out down to a water content of 0.5–25 wt. %, preferably 1 to 10 wt. %, and more preferably 1 to 8 wt. %, at temperatures which are conventionally in the range of 100–200° C.

There are no particular restrictions in respect of the particle form of the absorbent polymers according to the invention. The polymer can be present in the form of spheres, which have been obtained by inverse suspension polymerization, or in the form of irregularly shaped particles, which originate by drying and pulverization of the gel mass from the solution polymerization. The particle size is usually below 3,000 µm, preferably between 20 and 2,000 µm, and more preferably between 150 and 850 µm.

The after-crosslinking components according to the invention are applied in the form of their aqueous solutions. Suitable solvents are water and optionally polar, water-miscible organic solvents, which are slightly moist, such as, for example, acetone, methanol, ethanol or 2-propanol or mixtures thereof. The term aqueous solution in the context of the invention means, in respect of the solvent component, that in addition to the water it can also contain organic solvents. The concentration of the particular after-crosslinking component in the aqueous solvent can vary within wide limits and is in the range from 1 to 80 wt. %, preferably in the range from 5 to 65 wt. %, and more preferably in a range from 10 to 40 wt. %. The preferred solvent for the polyols as after-crosslinking agents or for the salt component is water, which is to be used in a total amount of 0.5-10 wt. %, preferably 0.75–5 wt. %, and more preferably 1.0–4 wt. %, based on the polymer.

A preferred solution comprises, for example, 1.5–3 parts by wt. of water, 0.5–1 part by wt. of polyol component and 0.4–0.6 part by wt. of an inorganic salt. The total amount of solvent is conventionally in the range of 0.5–12 wt. %, preferably 1–7 wt. %, and more preferably 1–5 wt. %, based on the polymer.

Depending on the solubility of the two components e) and f) of claim 1, the solution is heated from 20–100° C., preferably from 20–60° C., before application to the polymer. A separate, preferably simultaneous metering in of an aqueous solution of the polyol and an aqueous solution of the salt component is also possible if a homogeneous distribution of the two components on the polymer is ensured. Application of a single aqueous solution in which the two components are dissolved to the polymer is preferred.

The after-crosslinking agent solution should be mixed very thoroughly with the polymer particles. Suitable mixing units for application of the after-crosslinking agent solution are e.g. Patterson-Kelley mixers, DRAIS turbulence mixers, Lödige mixers, Ruberg mixers, screw mixers, plate mixers and fluidized bed mixers, as well as continuously operating vertical mixers in which the polymer powder is mixed by means of rotating blades at a high frequency (Schugi mixer). There is also the possibility of carrying out the coating of the polymer during a process step in the preparation of the polymer. The process of inverse suspension polymerization is particularly suitable for this.

After the after-crosslinking agent solution has been mixed with the polymer particles, the after-crosslinking reaction is carried out at temperatures in the range from at least 150° C. to 250° C., preferably 160° C. to 220° C., and more preferably 170° C. to 200° C. The optimum duration of the after-heating can easily be determined for the individual crosslinking agent types with a few experiments. It is limited by when the desired profile of properties of the superabsorber is destroyed again as a result of heat damage. The heat treatment can be carried out in conventional dryers or ovens; rotary tube ovens, fluidized bed dryers, plate dryers, paddle dryers or infra-red dryers may be mentioned by way of example.

The polymers according to the invention can be prepared continuously or discontinuously in a large-scale industrial manner by the abovementioned known process, the after-crosslinking according to the invention being carried out accordingly.

The polymers according to the invention can be employed for wide fields of use.

If they are used e.g. as absorbents in sanitary towels, nappies or in wound coverings, they have the property that they rapidly absorb large amounts of menstrual blood, urine or other body fluids. Since the agents according to the invention retain the absorbed liquids even under pressure and additionally are capable of distributing further liquid within the construction in the swollen state, they are more preferably employed in higher concentrations, in respect of the hydrophilic fiber material, such as e.g. fluff, than was hitherto possible. They are also suitable for use as a homogeneous superabsorber layer without a fluff content within the nappy construction, as a result of which particularly thin nappies are possible. The polymers are furthermore suitable for use in hygiene articles (incontinence products) for adults.

Such absorbent hygiene products as a rule have a general structure of a liquid-permeable cover (1) facing the body, a liquid-absorbing absorbent layer (2) and a substantially liquid-impermeable outer layer (3) facing away from the body. Further constructions are optionally also used for rapid absorption and distribution of body fluid (4) in the absorbent core. These constructions are often, but not necessarily, employed between the liquid-permeable cover (1) facing the body and the liquid-absorbing absorbent layer (2).

The liquid-permeable cover (1) as a rule comprises a nonwoven, fibrous fleece or another porous construction. Possible materials for this cover (1) are e.g. synthetic polymers, such as, for example, polyvinyl chloride or fluoride, polytetrafluoroethylene (PTFE), polyvinyl alcohols and derivatives, polyacrylates, polyamides, polyesters, polyurethanes, polystyrene, polysiloxanes or polyolefins (e.g. polyethylene (PE) or polypropylene (PP)) and naturally occurring fiber materials, as well as any desired combinations of the abovementioned materials in the sense of blended materials or composite materials or copolymers.

The liquid-permeable cover (1) has a hydrophilic character. It can furthermore comprise a combination of hydrophilic and hydrophobic constituents. A hydrophobic treatment of the liquid-permeable cover (1) is as a rule preferred, in order to allow rapid seepage times of body fluid into the liquid-absorbing absorbent layer (2), but partly hydrophobized covers (1) are also used.

The liquid-absorbing absorbent layer (2) comprises the superabsorbent powder or granules and optionally further components of, for example, fibrous materials, foamed materials, film-forming materials or porous materials, as well as combinations of two or more of these materials. Each of these materials can be of either natural or synthetic origin, or can have been prepared by chemical or physical modification of naturally occurring materials. The materials can be hydrophilic or hydrophobic, hydrophilic materials being preferred. This applies in particular to those compositions which are to efficiently absorb the body fluids secreted and transport them in the direction of regions of the absorbent core further removed from the entry point of the body fluid.

Suitable hydrophilic fiber materials are e.g. cellulose fibers, modified cellulose fibers (e.g. reinforced cellulose fibers), polyester fiber (e.g. Dacron), hydrophilic nylon and also hydrophilized hydrophobic fibers, such as e.g. surfactant-hydrophilized polyolefins (PE, PP), polyesters, polyacrylates, polyamides, polystyrene, polyurethanes and others.

Cellulose fibers and modified cellulose fibers are preferably employed. Combinations of cellulose fibers and/or modified cellulose fibers with synthetic fibers, such as e.g. PE/PP composite materials, so-called bi-component fibers, such as are used e.g. for thermobonding of airlaid materials, or other materials are also customary. The fiber materials can be in various use forms, e.g. as loose cellulose fibers separated out or laid out of an air stream or an aqueous phase, as nonwoven fleece or as tissue. Combinations of various use forms are possible.

Further pulverulent substances can optionally be employed in addition to the superabsorbent polymers according to the invention, such as e.g. odour-binding substances, such as cyclodextrins, zeolites, inorganic or organic salts and similar materials.

Polymer foams such as are described in the specifications DE 44 18 319 A1 and DE 195 05 709 A1 can be employed e.g. as porous materials and foamed materials.

Thermoplastic fibers (e.g. bi-component fibers of polyolefins), polyolefin granules, latex dispersions or hot-melt adhesives can be used for mechanical stabilization of the liquid-absorbing absorbent layer (2). One or more layers of tissue are optionally used for stabilization.

The liquid-absorbing absorbent layer (2) can be one layer or can comprise several layers. Constructions which comprise hydrophilic fibers, preferably cellulose fibers, optionally of a construction for rapid absorption and distribution of body fluid (4), such as, for example, chemically reinforced (modified) cellulose fibers or high loft fleeces of hydrophilic or hydrophilized fibers, and superabsorbent polymers can be used for this.

The superabsorbent polymers according to the invention can be distributed here homogeneously in the cellulose fibers or the reinforced cellulose fibers, but they can also be introduced as a layer between the cellulose fibers or the reinforced cellulose fibers, or the concentration of the superabsorbent polymers can have a gradient within the cellulose fibers or reinforced cellulose fibers. The ratio of the total amount of superabsorbent polymer and the total amount of cellulose fibers or reinforced cellulose fibers in the absorbing absorbent core can vary between 0–100 wt. %, in one embodiment concentrations of up to 100% of superabsorbent polymers being possible locally, e.g. with introduction of a gradient or introduction in layers. Such constructions with regions of high concentrations of absorbent polymers, wherein the content of polymer in certain regions is between 60 and 100 wt. %, preferably between 90 and 100 wt. %, are also described, for example, in the patent specification U.S. Pat. No. 5,669,894.

Several different superabsorbent polymers which differ, for example, in the rate of absorption, the permeability, the storage capacity, the absorption under pressure, the particle size distribution or the chemical composition can optionally be employed simultaneously. The various superabsorbers can be introduced into the absorbent cushion as a mixture with one another, or they can be placed in different locations in the absorbent core. Such a different placing can take place in the direction of the thickness of the absorbent cushion or of the length or width of the absorbent cushion.

The liquid-absorbing absorbent layer (2) comprises one or more of the layers comprising superabsorbent polymers according to the invention, optionally with cellulose fibers or reinforced cellulose fibers. In a preferred embodiment, constructions of combinations of layers with homogeneous introduction of the superabsorber and additionally introduction in layers are used.

The absorption articles can optionally have further layers of pure cellulose fibers or reinforced cellulose fibers on the side facing the body and/or also the side facing away from the body.

The structural possibilities described above can also be repeated several times, which can mean layering of two or more identical layers on top of one another or also layering of two or more different constructions of different structure on top of one another. The differences here lie in turn in the purely constructional nature or in the type of material used, such as e.g. the use of absorbent polymers according to the invention or with other polymers but different cellulose types.

The entire absorbent cushion or also individual layers of the liquid-absorbing absorbent layer (2) can optionally be separated by layers of tissue of other components of the absorption article or are in direct contact with other layers or components.

By way of example, the construction for rapid absorption and distribution of body fluid (4) and the liquid-absorbing absorbent layer (2), for example, can be separated from one another by tissue or can be in direct contact with one another. If no separate construction for rapid absorption and distribution of body fluid (4) exists between the liquid-absorbing absorbent layer (2) and the liquid-permeable cover (1) facing the body, but the effect of liquid distribution is to be achieved e.g. by the use of a specific liquid-permeable cover (1) facing the body, the liquid-absorbing absorbent layer (2) can also optionally be separated from the liquid-permeable cover (1) facing the body by a tissue.

Instead of tissue, nonwoven fleece can optionally also be introduced into the liquid-absorbing absorbent layer (2). Both components lead to the desired secondary effect of stabilization and strengthening of the absorption core in the moist state.

The liquid-absorbing absorbent layers, in particular fiber-containing liquid-distributing and -storing layers containing superabsorbent polymers, can be prepared by a diversity of preparation processes.

In addition to the established conventional processes, such as can be summarized under drum forming with the aid of shaping wheels, pockets and product moulds and correspondingly adapted metering devices for the raw materials, modern established processes, such as the airlaid process (e.g. EP 850 615, col. 4 line 39 to col. 5 line 29, U.S. Pat. No. 4,640,810) with all forms of metering, laying down of the fibers and bonding, such as hydrogen bonding (e.g. DE 197 50 890, col. 1 line 45 to col. 3 line 50), thermobonding, latex bonding (e.g. EP 850 615, col. 8 line 33 to col. 9 line 17) and hybrid bonding, the wetlaid process (e.g. PCT WO 99/49905, col. 4 line 14 to col. 7 line 16), carding, meltblown and spunblown processes and similar processes for the preparation of nonwovens containing superabsorber (in the context of the definition of EDANA, Brussels), also in combinations of these processes with one another, are to be understood as conventional methods for the preparation of the abovementioned liquid stores.

The preparation of laminates in the broadest sense and of extruded and coextruded, wet- and dry-bonded, as well as subsequently bonded, structures are possible as further preparation processes.

A combination of these possible processes with one another is also possible.

Chemically reinforced (modified) cellulose fibers or high loft fleeces of hydrophilic or hydrophilized fibers or a combination of the two can additionally be co-used, for example, for the production of absorption articles with a rapid absorption and distribution of body fluid (4).

Chemically reinforced, modified cellulose fibers can be produced, for example, from cellulose fibers which are converted in a chemical reaction by crosslinking agents, such as e.g. $C_2$-$C_8$ dialdehydes, $C_2$-$C_8$ monoaldehydes with an additional acid function or $C_2$-$C_9$ polycarboxylic acids. Specific examples are: glutaraldehyde, glyoxal, glyoxalic acid or citric acid. Cationically modified starch or polyamide-epichlorohydrin resins (e.g. KYMENE 557H, Hercules Inc., Wilmington, Del.) are also known. A twisted, crimped structure which has an advantageous effect on the rate of absorption of liquid is achieved and stabilized by the crosslinking.

The absorbent hygiene products can vary widely in their weight per unit area and thickness and therefore density. The densities of the regions of the absorption cores are typically between 0.08 and 0.25 g/cm$^3$. The weights per unit area are between 10 and 1,000 g/m$^2$, weights per unit area of between 100 and 600 g/m$^2$ preferably being realized (see also U.S. Pat. No. 5,669,894). The density varies over the length of the absorbent core. This occurs as a consequence of a controlled metering of the amount of cellulose fibers or reinforced cellulose fibers or of the amount of the superabsorbent polymer, since in preferred embodiments these components are introduced to a higher degree into the front region of the absorbent disposable article.

The polymers according to the invention are also employed in absorber articles which are suitable for further uses. For this, they are processed to a web by mixing with paper or fluff or synthetic fibers or by distributing the superabsorbent polymers between substrates of paper, fluff or non-woven textiles or by processing into carrier materials.

The polymers according to the invention are furthermore also used in all instances where aqueous liquids must be absorbed, such as e.g. in cable sheathings, in foodstuffs packaging, in the agricultural sector in plant growing and as a water store and as an active compound carrier with a time-delayed release of the active compound to the environment.

Surprisingly, the superabsorbent polymers according to the invention show a significant improvement in permeability, i.e. an improvement in the transportation of liquid in the swollen state. Polymers with permeability values (SFC) of up to $70 \cdot 10^{-7}$ cm$^3$ sec/g at a retention (TB) of at least 27 g/g are obtained, preferably polymers with SFC values of $>70 \cdot 10^{-7}$ to $\geq 150 \cdot 10^{-7}$ cm$^3$ sec/g at a retention (TB) of at least 25 g/g. In addition to these excellent SFC and retention values, the polymers according to the invention show measurement values for the absorption of liquid under pressure (AAP 0.7 psi) of at least 18 g/g.

The products according to the invention with this outstanding combination of properties of very high SFC values, high retention and high absorption under pressure can be prepared without the use of toxicologically unacceptable substances.

Test methods

For characterization of the absorbent polymers according to the invention, the retention (TB), absorption under pressure (AAP) and permeability to 0.9% sodium chloride solution in the swollen state (SFC) are determined.

a) The retention is stated according to the tea-bag method and as the mean of three measurements. About 200 mg polymer are welded into a tea-bag and immersed in 0.9% NaCl solution for 30 minutes. The tea-bag is then centrifuged in a centrifuge (23 cm diameter, 1,400 rpm) for 3 minutes and weighed. A tea-bag without water-absorbing polymer is also run as the blank value.

Retention=final weight-blank value value/amount weight out [g/g]

b) Absorption of liquid under pressure (AAP test according to EP 0 339 461).

The absorption under pressure (pressure load 50 g/cm$^2$) is determined by a method described in EP 0339461, page 7. Approx. 0.9 g superabsorber is weighed into a cylinder with a perforated base. The superabsorber layer uniformly sprinkled on is loaded with a plunger which exerts a pressure of 50 g/cm$^2$. The previously weighed cylinder is then placed on a glass filter plate in a dish containing 0.9% NaCl solution, in which the level of liquid corresponds exactly to the height of the filter plate. After the cylinder unit has been allowed to soak up 0.9% NaCl solution for 1 hour, this is re-weighed and the AAP is calculated as follows:

AAP=final weight (cylinder unit+superabsorber)-amount weighed out (cylinder unit+completely soaked superabsorber)/amount of superabsorber weighed out.

c) Permeability in the swollen state (SFC test according to WO 95/22356). Approx. 0.9 g superabsorber material is weighed into a cylinder with a perforated base and distributed carefully over the perforated surface. The superabsorber material is allowed to swell in JAYCO synthetic urine [composition: 2.0 g potassium chloride; 2.0 g sodium sulfate; 0.85 g ammonium dihydrogen phosphate; 0.15 g ammonium hydrogen phosphate; 0.19 g calcium chloride; 0.23 g magnesium chloride as anhydrous salts dissolved in 1 l distilled water] for 1 hour against a pressure of 20 g/cm$^2$. After the swollen height of the superabsorber has been recorded, 0.118 M NaCl solution is allowed to run from a levelled reservoir vessel through the swollen gel layer under a constant hydrostatic pressure. During the measurement, the swollen gel layer is covered with a special perforated cylinder which ensures a uniform distribution of the 0.118 M NaCl solution above the gel and constant conditions (measurement temperature 20–25° C.) during the measurement in respect of the nature of the gel bed. The pressure acting on the swollen superabsorber continues to be 20 g/cm$^2$. The amount of liquid which passes through the gel layer as a function of time is recorded at intervals of 20 seconds within a period of time of 10 minutes with the aid of a computer and a balance. The flow rate g/s through the swollen gel layer is determined by means of regression analysis with extrapolation of the gradient and determination of the middle point at time t=0 of the flow amount within minutes 2–10. The SFC value (K) is calculated as follows:

$$K = \frac{F_s(t=0) \cdot L_0}{r \cdot A \cdot \Delta P} = \frac{F_s(t=0) \cdot L_0}{139506}$$

wherein  $F_s(t=0)$  is the flow rate in g/s
 $L_0$  is the thickness of the gel layer in cm
 $r$  is the density of NaCl solution (1.003 g/cm$^3$)
 $A$  is the area of the upper side of the gel layer in the measuring cylinder (28.27 cm$^2$)
 $\Delta P$  is the hydrostatic pressure loading the gel layer (4,920 dyne/cm$^2$)
 and $K$ is the SFC value [cm$^3 \times$sec$\times$g$^{-1}$]

Formal addition of the numerical values of the tea-bag retention and the SFC value illustrates the sudden increase in this combination of properties in polymers according to the invention compared with untreated superabsorber powders or products which have been after-crosslinked on the surface by known methods. The numerical value is not achieved by a high contribution of one of the two values (e.g. a high TB retention value and a low SFC value and vice versa) in the products according to the invention.

EXAMPLES

In the examples and comparison examples, the powder envisaged for the surface crosslinking was in each case sieved off to a particle size of 150 μm to 850 μm.

Example 1

1.05 g polyethylene glycol (300) diacrylate and 1.35 g polyethylene glycol (750) monoallyl ether-acrylate, as the crosslinking agent, are dissolved in 965.115 g of an aqueous solution of sodium acrylate with a degree of neutralization of 70 mol % (monomer concentration: 37.7%). The monomer solution is flushed through with nitrogen in a polymerization vessel of plastic for 30 minutes in order to remove the dissolved oxygen. The polymerization is started at a temperature of 4° C. by successive addition of 0.3 g sodium peroxydisulfate in 10 g distilled water, 0.1 g 2,2'-azobis-2-amidinopropane dihydrochloride in 10 g distilled water, 0.07 g 35% hydrogen peroxide solution in 10 g distilled water and 0.015 g ascorbic acid in 2 g distilled water. When the end temperature (approx. 100° C.) was reached, the gel was comminuted with a meat chopper and dried for 2 h at 150° C. in a circulating air oven. The dried product was coarsely crushed and ground and the particles of size 150–850 μm were sieved out for further reaction (powder A).

50 g powder A were mixed with vigorous stirring with a solution of 0.5 g 1,3-propanediol, 1.25 g water and 0.25 g aluminium sulfate 18-hydrate and the mixture was then heated for 30 min in an oven which was temperature-controlled at 180° C. For comparison, 50 g powder A were mixed with a solution of 0.5 g 1.3-propanediol and 1.25 g water and the mixture was then heated for 30 min in an oven which was temperature-controlled at 130° C. (comparison example 1)

| Product | TB [g/g] | AAP$_{0.7}$ [g/g] | SFC [cm$^3$ s 10$^{-7}$/g] | TB + SFC |
|---|---|---|---|---|
| Powder A | 31.0 | | 0 | 31.0 |
| Example 1 | 26.0 | 22.6 | 130 | 156.0 |
| Comparison Example 1 | 27.0 | 24.0 | 40 | 67 |

Example 2

0.84 g triallylamine and 1.5 g polyethylene glycol (750) monoallyl ether-acrylate, as the crosslinking agent, are dissolved in 965.175 g of an aqueous solution of sodium acrylate with a degree of neutralization of 70 mol% (monomer concentration: 37.7%). The monomer solution is flushed through with nitrogen in a polymerization vessel of plastic for 30 minutes in order to remove the dissolved oxygen. The polymerization is started at a temperature of 4° C. by successive addition of 0.3 g sodium peroxydisulfate in 10 g distilled water, 0.1 g 2,2'-azobis-2-amidinopropane dihydrochloride in 10 g distilled water, 0.07 g 35% hydrogen peroxide solution in 10 g distilled water and 0.015 g ascorbic acid in 2 g distilled water. When the end temperature (approx. 100° C.) was reached, the gel was comminuted with a meat chopper and dried for 2 h at 150° C. in a circulating air oven. The dried product was coarsely crushed and ground and the particles of size 150–850 μm were sieved out for further reaction (powder B).

50 g powder B were mixed with vigorous stirring with a solution of 0.25 g aluminium sulfate 18-hydrate and 0.25 g water and then with a solution of 0.5 g ethylene glycol and 0.5 g water and the mixture was then heated for 60 min in an oven which was temperature-controlled at 170° C. (example 2).

50 g powder B were mixed with vigorous stirring with a solution of 0.5 g glycerol, 0.05 g ethylene glycol diglycidyl ether and 1.25 g water and the mixture was then heated for 60 min in an oven which was temperature-controlled at 170° C. (comparison example 2).

50 g powder B were mixed with vigorous stirring with a solution of 0.25 g glycerol, 0.25 g ethylene glycol diglycidyl ether and 1.25 g water and the mixture was then heated for 60 min in an oven which was temperature-controlled at 170° C. (comparison example 3).

50 g powder B were mixed with vigorous stirring with a solution of 0.25 g ethylene glycol, 0.25 g ethylenediamine and 1.25 g water and the mixture was then heated for 60 min in an oven which was temperature-controlled at 170° C. (comparison example 4).

| Product | TB [g/g] | AAP$_{0.7}$ [g/g] | SFC [cm$^3$ s $10^{-7}$/g] | TB + SFC |
|---|---|---|---|---|
| Powder B | 30.5 | | 0 | 30.5 |
| Example 3 | 26.5 | 23.5 | 60 | 86.5 |
| Comparison example 3 | 26.0 | 23.5 | 35 | 61.0 |
| Comparison example 4 | 26.4 | 24.0 | 33 | 59.4 |
| Comparison example 5 | 27.0 | 23.5 | 10 | 37.0 |

Industrial applicability

The examples described for the process according to the invention all show a very good overall performance, in particular in respect of retention and permeability. Free-flowing coated powders which can easily be metered are obtained. The use of small amounts of solution for coating and the omission of organic solvents, inorganic powders or other auxiliary substances allows an economical and reliable production process. A significant improvement in permeability with a simultaneously high retention is to be achieved exclusively by combination of organic after-crosslinking agent and the salt component.

What is claimed:

1. Pulverulent polymer which is after-crosslinked on the surface, absorbs water, aqueous or serous liquids and bloods and comprises from
   a) 55–99.9% wt. % of polymerized, ethylenically unsaturated monomers which contain acid groups and are neutralized to the extent of at least 25 mol %,
   b) 0–40 wt. % of polymerized, ethylencially unsaturated monomers which can be copolymerized with a),
   c) 0.1–5.0 wt. % of one or more polymerized-in crosslinking agents,
   d) 0–30 wt. % of a water-soluble polymer the sum of the amounts by weight of a) to d) being 100 wt. %, wherein the polymer has been coated with
   e) 0.01 to 5 wt. %, based on the polymer, of at least one polyol as an agent for after-crosslinking of the surface in an aqueous solution; and
   f) 0.001–1.0 wt. %, based on the polymer, of a cation in the form of a salt dissolved in an aqueous solution and has been heated to an after-crosslinking temperature in the range of at least 150 to 250° C., the weight ratio of the salt to the polyol being in the range from 1:0.8 to 1:4 and the total amount of aqueous solutions having been 0.5 to 10 wt. %, based on the polymer, excluding crosslinked partly neutralized polyacrylic acids which have been treated with Al$_2$(SO$_4$)$_3$ and glycerol in a weight ratio of 1:1 or with Al$_2$(SO$_4$)$_3$ 16H$_O$ and polyethylene glycol in a weight ration of 1:1.8 or with Al$_2$(SO$_4$)$_3$·14H$_2$O and ethylene glycol in a weight ratio of 1:2 or with Al$_2$(SO$_4$)$_3$·18H$_2$O and ethylene glycol in a weight ratio of 1:2 or Al$_2$(SO$_4$)$_3$19 18H$_2$O and propylene glycol in a weight ratio of 1:1.6.

2. Polymer according to claim 1 wherein component e) is employed in an amount of 0.1 to 2.5 wt. %, 0.5 to 1.5 wt. %, and component f) is employed in an amount of 0.005 to 0.5 wt. %.

3. Polymer according to claim 1 wherein the weight ratio of salt to polyol is in the range from 1:1 to 1:3.5.

4. Polymer according to claim 1 wherein only water has been employed as the solvent for components e) and f).

5. Polymer according to claim 1 wherein components e) and f) have been employed together in an aqueous solution.

6. Polymer according to claim 1 wherein the total amount of water of the aqueous solutions added separately or together was 0.75 to 5 wt. %, based on the polymer.

7. Polymer according to claim 1 wherein as component f), the cation originates from an alkali metal or alkaline earth metal salt, a salt of zinc, iron, aluminum, titanium or another transition metal salt or from a double salt of two different cations or a mixture of the salts, preferably an inorganic, water-soluble aluminum salt.

8. Polymer according to claim 1 wherein $C_2$-$C_8$-alkylene diols, $C_2$-$C_8$-alkylene triols, hydroxy compounds of higher functionality and/or di- and polyalkylene glycols have been employed as the polyols.

9. Polymer according to claim 1 wherein the after-crosslinking has been carried out at temperatures of 160° C. to 220° C.

10. Polymer according to claim 1 wherein at least 50 wt. % of the acid groups of the monomer units a) are carboxyl groups.

11. Polymer according to claim 1 wherein the monomer units a) are derived from acrylic acid and/or methacrylic acid.

12. Polymer according to claim 1 wherein starch and/or polyvinyl alcohol or derivatives thereof have been employed as component d).

13. Polymer according to claim 1 wherein the polymer has a retention (TB) of at least 26 g/g at a permeability (SFC) of up to 70·10$^{-7}$ cm$^3$ sec/g.

14. Polymer according to claim 1 wherein the polymer has a retention (TB) of at least 25 g/g at a permeability (SFC) of >70·10$^{-7}$ to 150·10–7 cm$^3$ sec/g.

15. Polymer according to claim 13 wherein the polymer has an absorption of liquid under pressure (AAP 0.7) of at least 18 g/g.

16. Process for the preparation of absorbent polymers according to claim 1 wherein a mixture of
a) 55–99.9 wt. % of ethylenically unsaturated monomers which carry acid groups and are neutralized to the extent of at least 25 mol %,
b) 0–40 wt. % of ethylencially unsaturated monomers which can be copolymerized with a),
c) 0.1–5.0 wt. % of one or more crosslinking compounds,
d) 0–30 wt. % of a water-soluble polymer the sum of components a) to d) being 100 wt. %, is subjected to polymerization and the product is optionally comminuted, dried, pulverized and sieved, and in that the polymer powder is treated with
e) 0.01 to 5 wt. %, based on the polymer, of at least one polyol as an agent for after-crosslinking of the surface in the form of an aqueous solution and with
f) 0.001–1.0 wt. %, based on the polymer, of a cation of a salt dissolved in an aqueous solution,
the total amount of water being 0.5–10 wt. %, based on the polymer, and the weight ratio of salt to polyol being in the range from 1:0.8 to 1:4, wherein an intensive mixing of the aqueous solutions, present together or separately, of components e) and f) with the polymer powder is carried out simultaneously or successively and thermal after-crosslinking of the polymer powder is carried out by subsequent heating to >150° C. to 250° C.

17. Process according to claim 16 wherein the polymer powder employed for the after-crosslinking has a residual moisture content of 0.5 to 25 wt. %.

18. Process according to claim 16 wherein the polymer powder employed has a particle size of <3,000 µm.

19. Process according to claim 16 wherein the aqueous solutions of components e) and f) are heated up to 20° C. to 100° C.

20. Process according to claim 16 wherein the after-crosslinking is carried out at temperatures of 160° to 220° C.

21. Use of the polymers according to one of claim 1 as absorbents for water or aqueous liquids, preferably in constructions for absorption of body fluids, in foamed and non-foamed sheet-like structures, in packaging materials, in constructions for plant growing, as soil improvement agents or as active compound carriers.

22. Use of the polymers according to claim 1 as the predominant or sole absorbent in absorbent inserts.

* * * * *

UNITED STATES PATENT AND TRADEMARK OFFICE
CERTIFICATE OF CORRECTION

PATENT NO. : 6,831,142 B2  
DATED : December 14, 2004  
INVENTOR(S) : Richard Mertens and Harren Jörg It is certified that error appears in the above-identified patent and that said Letters Patent is hereby corrected as shown below:

Column 2,
Line 27, "DE-A40 20 780" should read -- DE-A-40 20 780 --;

Column 4,
Line 58, "$Al_2(SO_4)_3.14H_2O$" should read -- $Al_2(SO_4)_3 \cdot 14H_2O$ --;
Line 59, "$Al_2(SO_4)_3.18H_2O$" should read -- $Al_2(SO_4)_3 \cdot 18H_2O$ --;

Column 6,
Line 16, "$Al_2(SO_4)_3 x14. 18H_2O$" should read -- $Al_2(SO_4)_3 x14-18H_2O$ --;

Column 13,
Line 42, "11" should read -- 1 l --;

Column 16,
Line 19, "$Al_2(SO_4)_3 16H$" should read -- $Al_2(SO_4)_3 \cdot 16H_2O$ --;
Line 20, "ration" should read -- ratio --; and
Line 64, "$150 \cdot 10\text{-}7 \; cm^3 sec/g$" should read -- $150 \cdot 10^{-7} \; cm^3 sec/g$ --.

Signed and Sealed this

Tenth Day of May, 2005

JON W. DUDAS
*Director of the United States Patent and Trademark Office*